US009351928B2

(12) United States Patent
Staniforth et al.

(10) Patent No.: US 9,351,928 B2
(45) Date of Patent: *May 31, 2016

(54) METHOD OF MAKING PARTICLES FOR USE IN A PHARMACEUTICAL COMPOSITION

(75) Inventors: John Nicholas Staniforth, Bath (GB); David Alexander Vodden Morton, Bath (GB); Rossella Musa, Parma (IT)

(73) Assignee: VECTURA LIMITED, Wiltshire (GB)

(*) Notice: Subject to any disclaimer, the term of this patent is extended or adjusted under 35 U.S.C. 154(b) by 0 days.

This patent is subject to a terminal disclaimer.

(21) Appl. No.: 12/782,283

(22) Filed: May 18, 2010

(65) Prior Publication Data
US 2010/0285142 A1 Nov. 11, 2010

Related U.S. Application Data

(63) Continuation of application No. 10/312,488, filed as application No. PCT/GB01/02860 on Jun. 27, 2001, now Pat. No. 7,744,855.

(30) Foreign Application Priority Data

Jun. 27, 2000 (GB) .................................. 00113608.4
Nov. 30, 2000 (GB) .................................. 0029263.1
Apr. 17, 2001 (GB) .................................... 01/01732

(51) Int. Cl.
*A61K 9/16* (2006.01)
*A61K 9/14* (2006.01)
*A61K 31/167* (2006.01)
*A61K 31/58* (2006.01)
*A61K 9/00* (2006.01)
*A61K 31/573* (2006.01)

(52) U.S. Cl.
CPC ............... *A61K 9/0075* (2013.01); *A61K 9/145* (2013.01); *A61K 31/167* (2013.01); *A61K 31/573* (2013.01); *A61K 31/58* (2013.01); *Y10S 514/958* (2013.01)

(58) Field of Classification Search
CPC ... A61K 9/0075; A61K 31/167; A61K 9/145; A61K 31/58
IPC .................. A61K 9/0075, 31/167, 9/145, 31/58
See application file for complete search history.

(56) References Cited

U.S. PATENT DOCUMENTS

| | | | |
|---|---|---|---|
| 4,349,542 A | 9/1982 | Staniforth | |
| 5,376,386 A | 12/1994 | Ganderton | |
| 5,506,203 A | 4/1996 | Backstrom | |
| 5,612,053 A | 3/1997 | Baichwal | |
| 5,908,639 A * | 6/1999 | Simpkin et al. | 424/489 |
| 5,952,008 A | 9/1999 | Backstrom | |
| 6,153,224 A * | 11/2000 | Staniforth | 424/490 |
| 6,428,814 B1 | 8/2002 | Bosch | |
| 6,475,523 B1 | 11/2002 | Staniforth | |
| 6,518,239 B1 | 2/2003 | Kuo | |
| 6,521,260 B1 * | 2/2003 | Staniforth | 424/490 |
| 6,645,466 B1 * | 11/2003 | Keller et al. | 424/43 |
| 6,655,379 B2 | 12/2003 | Clark | |
| 6,884,794 B2 * | 4/2005 | Staniforth et al. | 514/170 |
| 7,011,818 B2 * | 3/2006 | Staniforth | 424/45 |
| 7,223,748 B2 * | 5/2007 | Staniforth et al. | 514/174 |
| 7,541,022 B2 * | 6/2009 | Staniforth et al. | 424/46 |
| 7,718,163 B2 * | 5/2010 | Staniforth | 424/46 |
| 7,744,855 B2 * | 6/2010 | Staniforth et al. | 424/45 |
| 8,182,791 B2 * | 5/2012 | Staniforth et al. | 424/45 |
| 8,871,274 B2 * | 10/2014 | Staniforth et al. | 424/490 |
| 2003/0165436 A1 | 9/2003 | Staniforth | |
| 2003/0175214 A1 * | 9/2003 | Staniforth et al. | 424/46 |
| 2003/0185764 A1 | 10/2003 | Staniforth | |
| 2004/0037785 A1 | 2/2004 | Staniforth | |
| 2004/0047810 A1 | 3/2004 | Staniforth | |
| 2004/0071635 A1 | 4/2004 | Staniforth | |
| 2005/0152849 A1 | 7/2005 | Staniforth | |
| 2006/0147389 A1 | 7/2006 | Staniforth | |
| 2010/0330188 A1 * | 12/2010 | Staniforth | 424/493 |
| 2011/0184088 A1 | 7/2011 | Lohmeijer | |
| 2011/0294987 A1 | 12/2011 | Kanazaki | |

FOREIGN PATENT DOCUMENTS

| | | |
|---|---|---|
| AU | 756852 | 6/2000 |
| CA | 2 017 851 | 5/1990 |
| CA | 2347856 | 5/2005 |
| EP | 0260241 | 3/1988 |
| EP | 0606486 * | 7/1994 |
| EP | 0824344 | 2/1998 |
| EP | 1 064 942 | 1/2001 |
| EP | 1169065 | 3/2005 |
| EP | 1549410 | 1/2007 |

(Continued)

OTHER PUBLICATIONS

Japanese Patent Office Official Letter of Refusal, dated Aug. 23, 2011.
Hallworth et al. "The twin impinger: a simple device for assessing the delivery of drugs from metered dose pressurized aerosol inhalers." J. Pham. Pharmacol. 1987, 39: 966-972.
Fransen, "Studies on a Novel Powder Formulation for Nasal Drug Delivery." Digital Comprehensive Summaries of Uppsala Dissertations from the Faculty of Pharmacy, Uppsala University (2008).
Kassem, "Generation of deeply inspirable clouds from dry powder mixtures." University of London, pp. 2-9, 161-198, 1990.
Lucas et al., "Enhancement of small particle size dry powder aerosol formulations using an ultra low density additive." Pharmaceutical Research 1999, 16(10), 1643-1647.

(Continued)

*Primary Examiner* — Mina Haghighatian
(74) *Attorney, Agent, or Firm* — Matthew S. Gibson; Reed Smith LLP

(57) ABSTRACT

A method for making composite excipient particles for use in a pharmaceutical composition comprises a milling step in which particles of an excipient material are milled in the presence of an additive material. The product particles are of small size and the milling requires relatively low input of time and energy. The composite particles are suitable for use in inhalable pharmaceutical compositions.

19 Claims, No Drawings

(56) References Cited

FOREIGN PATENT DOCUMENTS

| | | | |
|---|---|---|---|
| GB | 2269992 | * | 3/1994 |
| WO | 8705213 | | 9/1987 |
| WO | WO 8705213 | * | 9/1987 |
| WO | 8801862 | | 3/1988 |
| WO | WO 94/04133 | | 3/1994 |
| WO | 9623485 | | 8/1996 |
| WO | WO 9623485 | * | 8/1996 |
| WO | WO 97/03649 | | 2/1997 |
| WO | 9831346 | | 7/1998 |
| WO | 9835800 | | 8/1998 |
| WO | 0028979 | | 3/2000 |
| WO | WO 0028979 | * | 5/2000 |
| WO | 0033789 | | 6/2000 |
| WO | 0033811 | | 6/2000 |
| WO | 0178693 | | 10/2001 |
| WO | 0178695 | | 10/2001 |
| WO | 2011140307 | | 11/2011 |

OTHER PUBLICATIONS

Lucas et al., "Protein Deposition from Dry Powder Inhalers: Fine Particle Multiplets as Performance Modifiers." Pharm. Research, vol. 15, No. 4, 1998.

Ganderton, "The Generation of Respirable Clouds Form Coarse Powder Aggregates." Journal of Biopharmaceutical Sciences 3: 1-2; 101-105 (1992).

Podczeck, "The Influence of Particle Size Distribution and Surface Roughness of Carrier Particles on the in vitro Properties of Dry Powder Inhalations." Aerosol Science and Technology 31; 301-212 (1999).

Kawashima et al. "Effect of surface morphology of carrier lactose on dry powder inhalation property of pranlukast hydrate." International Journal of Pharmaceutics 172; 179-188 (1998).

* cited by examiner

METHOD OF MAKING PARTICLES FOR USE IN A PHARMACEUTICAL COMPOSITION

This application is a continuation application of U.S. patent application Ser. No. 10/312,488, filed Mar. 11, 2003, which is a national stage application of PCT/GB01/02860, filed Jun. 27, 2001, the disclosures of which are hereby incorporated by reference in their entireties.

The present invention relates to particles and to methods of making particles. In particular, the invention relates to methods of making composite excipient particles comprising a pharmaceutical excipient material.

It is known to administer to patients drugs in the form of fine particles. For example, in pulmonary administration a particulate medicament composition is inhaled by the patient. Pulmonary administration is particularly suitable for medicaments which are intended to cure or alleviate respiratory conditions such as asthma and for medicaments which are not suitable for oral ingestion such as certain biological macromolecules. Known devices for the administration of drugs to the respiratory system include pressurised metered dose inhalers (pMDI's) and dry powder inhalers (DPI's).

In order that the particles be carried deep into the lungs, the particles must be very fine, for example having a mass median aerodynamic diameter of less than 10 µm.

Such small particles are, however, thermodynamically unstable due to their high surface area to volume ratio, which provides significant excess surface free energy and encourages particles to agglomerate. In the inhaler, agglomeration of small particles and adherence of particles to the walls of the inhaler are problems that result in the active particles leaving the inhaler as large agglomerates or being unable to leave the inhaler and remaining adhered to the interior of the inhaler.

In an attempt to improve that situation, dry powders for use in dry powder inhalers often include particles of an excipient material mixed with the fine particles of active material. Such particles of excipient material may be coarse, for example, having mass median aerodynamic diameters greater than 90 µm, (such coarse particles are referred to as carrier particles) or they may be fine.

The step of dispersing the active particles from other active particles and from the carrier particles, if present, to form an aerosol of fine active particles for inhalation is significant in determining the proportion of the dose of active material which reaches the desired site of absorption in the lungs. In order to improve the efficiency of that dispersal it is known to include in the composition additive materials. Such additive materials are thought to reduce the attractive forces between the particles thereby promoting their dispersal.

WO 97/23485 discloses powders for inhalation comprising carrier particles and an additive material for the promotion of the dispersal of the active particles from the carrier particles. The use of gentle milling of carrier particles of diameter 90 to 125 µm in order to remove surface asperities which are suggested to be sites of high surface energy at which active particles can be bound so tightly to the carrier particles that they are not released upon actuation of the inhaler is also disclosed. In some cases the carrier particles are gently milled in the presence of the additive material. However, in all cases, the milling treatment is a gentle one such that the size of the carrier particles is not substantially changed.

The present invention provides a method for making composite excipient particles for use in a pharmaceutical composition, the method comprising a milling step in which particles of an excipient material are milled in the presence of an additive material.

The additive material is an material which, when included in a dry powder formulation for inhalation, promotes the dispersal of the particles, particularly the active particles, to form an aerosol upon actuation of the inhaler. Additive materials and dry powder formulations containing the additive materials are disclosed in WO 97/23485. The additive materials are, in particular, suitable for promoting the release (upon actuation of the inhaler) of the active particles from carrier particles when a dry powder comprising active particles, carrier particles and additive material is administered via a dry powder inhaler.

It will be understood that the additive material will be a different material to the excipient material.

It has been found that the milling of the particles of excipient material in the presence of an additive material produces significantly smaller particles and/or requires less time and less energy than the equivalent process carried out in the absence of the additive material. Using the method of the invention, it has been possible to produce composite excipient particles which have a mass median aerodynamic (MMAD) or a volume median diameter (VMD) of less than 1 µm. It is often not possible to make such small particles by other milling methods. Furthermore, when the composite excipient particles are included in a pharmaceutical composition the additive material promotes the dispersal of the active particles on administration of that composition to the patient, for example, via actuation of a dry powder inhaler device. ("Actuation of a dry powder inhaler device" refers to the process during which a dose of the powder is removed from its rest position in the inhaler device, usually by a patient inhaling. That step takes place after the powder has been loaded into the dry powder inhaler device ready for use.) The degree of that promotion of dispersal has been found to be enhanced in comparison to a composition made by simple blending of similar sized particles of excipient material with additive material. This is believed to be because the method of the invention produces improved distribution of the additive material on the surfaces of the excipient particles.

The particles of excipient material may comprise more than 50% by weight of excipient material, preferably more than 80% by weight, more preferably more than 95% by weight of excipient material. The particles of excipient material preferably consists essentially of excipient material.

The method of the invention produces composite excipient particles.

The composite excipient particles are particles of excipient material which have, upon their surfaces, an amount of the additive material. That amount of additive material may be very small, for example, in the case where the additive material is present as a solution which is removed after the milling step leaving only a residue of additive material upon the surface of the active or excipient particles.

The additive material may be in the form of a coating on the surfaces of the particles of excipient material. The coating may be a discontinuous coating. The additive material may be in the form of particles adhering to the surfaces of the particles of excipient material.

The pharmaceutical composition may be any pharmaceutical composition which comprises an excipient material in the form of small particles, for example, particles of mass median aerodynamic diameter of less than 50 µm.

The word "milling" as used herein refers to any mechanical process which applies sufficient force to the particles of excipient material that it is capable of breaking coarse particles (for example, particles of mass median aerodynamic diameter greater than 100 µm) down to fine particles of mass median aerodynamic diameter not more than 50 µm. For example, the milling step may be one which if the excipient particles were replaced with the same weight of lactose having a MMAD of between 150 and 200 µm would be capable of reducing the MMAD of that lactose to below 50 µm. It has been found that processes which do not apply that degree of force are not effective in the method of the invention. It is believed that is because that degree of force is required to separate the individual particles of excipient material such that effective mixing and effective application of the additive material to the surfaces of those particles is achieved. It should be understood, however, that in the case where the particles of excipient material are already fine, for example, having a mass median aerodynamic diameter below 60 µm prior to the milling step, the size of those particles may not be significantly reduced. The important thing is that the milling process applies a sufficiently high degree of force or energy to the particles.

A wide range of milling devices and conditions are suitable for use in the method of the invention. The selection of appropriate milling conditions, for example, intensity of milling and duration, to provide the required degree of force will be within the ability of the skilled person who will understand how to arrange those milling conditions such that the milling is capable of breaking down coarse particles, as mentioned above. Ball milling is a preferred method. Alternatively, a high pressure homogeniser may be used in which a fluid containing the particles is forced through a valve at high pressure producing conditions of high shear and turbulence. Shear forces on the particles, impacts between the particles and machine surfaces or other particles and cavitation due to acceleration of the fluid may all contribute to the fracture of the particles. Such homogenisers may be more suitable than ball mills for use in large scale preparations of the composite excipient particles. Suitable homogensiers include the EmulsiFlex high pressure homogeniser which is capable of pressure up to 4000 Bar, Niro Soavi high pressure homogenisers (capable of pressures up to 2000 Bar), and the Microfluidics Microfluidiser (maximum pressure 2750 Bar). The milling step may, alternatively, involve an agitator bead mill, for example, the DYNO-mill (Willy A. Bachofen AG, Switzerland) or the Netzsch high energy media mill. The Mechano-Fusion system (Hosokawa Micron Ltd) and the Hybridizer (Nara) are also suitable for use with the invention. Other possible milling devices include air jet mills, pin mills, hammer mills, knife mills and ultracentrifugal mills. Preferably, the milling process is a sealed process, preventing the escape of the additive material as fine particles or as a vapour. Jet milling may be used but in some cases additive material can be lost from the jet mill, for example, when the additive material is of very small particles, e.g. less than 1 µm in diameter.

Where the excipient material is in the form of coarse particles prior to the milling step their size will be substantially reduced during the milling step.

The mass median aerodynamic diameter of the particles of excipient material may be substantially reduced during the milling step. More preferably the mass median aerodynamic diameter (MMAD) of the particles of excipient material is reduced 10%, advantageously by at least 20%, preferably by at least 50%, more preferably by at least 70% during the milling step.

After the milling step, the mass median aerodynamic diameter of the composite excipient particles is preferably not more than 50 µm, advantageously not more than 20 µm, more preferably not more than 15 µm and especially preferably not more than 10 µm. Furthermore, 90% by weight of the composite excipient particles may have a diameter of less than 50 µm, advantageously less than 20 µm, more preferably less than 15 µm and especially preferably less than 10 µm. The mass median aerodynamic diameter of the composite excipient particles will, in general not be less than 0.1 µm.

The milling step may be carried out in a closed vessel, for example in a ball mill. The use of a closed vessel prevents loss of ultrafine particles or vapour of the additive material which has been found to occur in jet milling or other open processes. The milling may be dry, that is to say, there is no liquid present and the mixture to be milled is in the form of a dry particulate. Preferably, the milling is wet, that is, the milling step is carried out in the presence of a liquid. The liquid medium may be aqueous or non-aqueous, high or low volatility and of any solid content as long as it does not dissolve the excipient particles to any significant degree and its viscosity is not so high that it prevents motion of the balls. The additive material is preferably not dissolved in the liquid but is present in the form of particles. However, the additive material may be soluble in the liquid medium in which case it will be present as a solution during the milling step and will adsorb to the particle surfaces. The presence of a liquid medium helps to prevent compacting of the particles of excipient material on the walls of the vessel and may also allow the more even spreading of the additive material on the surface of the particles of excipient material as compared to dry milling. Preferably, the method also comprises the step of removing the liquid after the milling step. That may be accomplished by sieving followed by spray drying, or by evaporation of the liquid (followed by milling, if necessary, to break up large aggregates or cakes of material or by freeze drying). Preferably, the liquid is removed by spray drying.

As mentioned above, the composite excipient particles produced after the milling step may be of a suitable size for use in a pharmaceutical composition, for example, a powder or suspension for inhalation. However, it may also be desirable for the composite excipient particles to be smaller than that and to have after the milling step an agglomeration step in which the particles of excipient material are agglomerated to form agglomerated particles. In that way agglomerates of a size tailored to the requirement may be produced. Preferably, the agglomeration step is a spray drying step. The spray drying conditions may be selected to produce droplets having a desired size in the range of 1000 µm to 0.5 µm. The size of the agglomerates produced will depend largely on the concentration of the composite excipient particles in the spray feed and the droplet size. Other materials, for example, binders may be included in the spray feed. Where the milling step is wet milling, the suspension or slurry may be spray dried directly after the milling step. Agglomeration may also be conducted in a fluid bed dryer or granulator.

The optimum amount of additive material will depend on the chemical composition and other properties of the additive material and upon the nature of the excipient material. In general, the amount of additive material in the composite particles will be not more than 60% by weight, based on the weight of the excipient material. However, it is thought that for most additive materials the amount of additive material should be in the range of 40% to 0.25%, preferably 30% to 0.5%, more preferably 20% to 2%, based on the total weight of the additive material and the excipient material being milled. In general, the amount of additive material is at least 0.01% by weight based on the total weight of the additive material and the excipient material being milled.

Where additive material is lost in the process, for example, as particles carried away in the filtrate when a liquid milling medium is filtered off, it may be necessary to add more additive material at the start of the milling step than is desired in the composite excipient particles.

Advantageously the additive material is an anti-adherent material and will tend to decrease the cohesion between the composite excipient particles and between the composite excipient particles and any other particles present in the pharmaceutical composition.

Advantageously the additive material is an anti-friction agent (glidant) and will give better flow of the pharmaceutical composition in, for example, a dry powder inhaler which will lead to a better dose reproducibility.

Where reference is made to an anti-adherent material, or to an anti-friction agent, the reference is to include those materials which are able to decrease the cohesion between the particles, or which will tend to improve the flow of powder in an inhaler, even though they may not usually be referred to as anti-adherent material or an anti-friction agent. For example, leucine is an anti-adherent material as herein defined and is generally thought of as an anti-adherent material but lecithin is also an anti-adherent material as herein defined, even though it is not generally thought of as being anti-adherent, because it will tend to decrease the cohesion between the composite excipient particles and between the composite excipient particles and any other particles present in the pharmaceutical composition.

Advantageously, the additive material consists of physiologically acceptable material.

The additive material may include a combination of one or more materials.

It will be appreciated that the chemical composition of the additive material is of particular importance. Preferably, the additive material is a naturally occurring animal or plant substance.

Advantageously, the additive material includes one or more compounds selected from amino acids and derivatives thereof, and peptides and polypeptides having molecular weight from 0.25 to 1000 Kda, and derivatives thereof. Amino acids, peptides or polypeptides and derivatives of peptides and polypeptides are both physiologically acceptable and give acceptable release of the active particles on inhalation.

It is particularly advantageous for the additive material to comprise an amino acid. The additive material may comprise one or more of any of the following amino acids: leucine, isoleucine, lysine, valine, methionine, phenylalanine. The additive may be a salt or a derivative of an amino acid, for example aspartame or acesulfame K. Preferably, the additive particles consist substantially of an amino acid, more preferably of leucine, advantageously L-leucine. The D- and DL- forms may also be used. As indicated above, leucine has been found to give particularly efficient dispersal of the active particles on inhalation.

The additive material may include one or more water soluble substances. This helps absorption of the substance by the body if the additive reaches the lower lung. The additive material may include dipolar ions, which may be zwitterions.

Alternatively, the additive material may comprise a phospholipid or a derivative thereof. Lecithin has been found to be a good material for the additive material.

Preferably, the additive material comprises a metal stearate, or a derivative thereof, for example, sodium stearyl fumarate or sodium stearyl lactylate. Advantageously, the additive material comprises a metal stearate. For example, magnesium stearate, calcium stearate, sodium stearate or lithium stearate. Preferably, the additive material comprises magnesium stearate.

The additive material may include or consist of one or more surface active materials, in particular materials that are surface active in the solid state, which may be water soluble, for example lecithin, in particular soya lecithin, or substantially water insoluble, for example solid state fatty acids such as oleic acid, lauric acid, palmitic acid, stearic acid, erucic acid, behenic acid, or derivatives (such as esters and salts) thereof such as glyceryl behenate. Specific examples of such materials are: phosphatidylcholines, phosphatidylglycerols and other examples of natural and synthetic lung surfactants; Liposomal formulations; lauric acid and its salts, for example, sodium lauryl sulphate, magnesium lauryl sulphate; triglycerides such as Dynsan 118 and Cutina HR; and sugar esters in general.

Other possible additive materials include talc, titanium dioxide, aluminium dioxide, silicon dioxide and starch.

The additive material preferably comprises one or more materials selected from the group consisting of amino acids, lecithins, phospholipids and metal stearates (especially magnesium stearate).

It should be understood that, whilst the above discussion of the additive material has related primarily to the use of those additive materials in pharmaceutical compositions for dry powder inhalers, the composite excipient particles of the present invention are suitable for use in any pharmaceutical composition which requires the dispersal of small particles of active material into an aerosol cloud. The composite excipient particles are therefore especially suitable for use in pharmaceutical compositions which are administered as an aerosol or cloud. Such compositions include powders for dry powder inhalers, suspensions for use in pressurised metered dose inhalers.

The terms "active particles" and "particles of active material" are used interchangeably herein. The active particles referred to throughout the specification will comprise one or more pharmacologically active agents. The active particles advantageously consist essentially of one or more pharmacologically active agents. Suitable pharmacologically active agents may be materials for therapeutic and/or prophylactic use. Active agents which may be included in the formulation include those products which are usually administered orally by inhalation for the treatment of disease such as respiratory disease, for example, β-agonists.

The active particles may comprise at least one $\beta_2$-agonist, for example one or more compounds selected from terbutaline, salbutamol, salmeterol and formoterol. If desired, the active particles may comprise more than one of those active agents, provided that they are compatible with one another under conditions of storage and use. Preferably, the active particles are particles of salbutamol sulphate. References herein to any active agent are to be understood to include any physiologically acceptable derivative. In the case of the $\beta_2$-agonists mentioned above, physiologically acceptable derivatives include especially salts, including sulphates.

The active particles may be particles of ipatropium bromide.

The active particles may include a steroid, which may be beclometasone dipropionate or may be fluticasone. The active principle may include a cromone which may be sodium cromoglycate or nedocromil. The active principle may include a leukotriene receptor antagonist.

The active particles may include a carbohydrate, for example heparin.

The active particles may advantageously comprise a therapeutically active agent for systemic use being advantageously capable of being absorbed into the circulatory system via the lungs. For example, the active particles may comprise peptides or polypeptides or proteins such as DNase, leukotrienes or insulin (including substituted insulins and pro-insulins), cyclosporin, interleukins, cytokines, anti-cytokines and cytokine receptors, vaccines (including influenza, measles, 'anti-narcotic' antibodies, meningitis), growth hormone, leuprolide and related analogues, interferons, desmopressin, immunoglobulins, erythropoeitin, calcitonin and parathyroid hormone. The pharmaceutical compositions of the invention may in particular have application in the administration of insulin to diabetic patients, thus avoiding the normally invasive administration techniques used for that agent.

The composite excipient particles of the invention may advantageously be for use in pain relief. Non-opioid analgesic agents that may be included as pain relief agents are, for example, alprazolam, amitriptyline, aspirin, baclofen, benzodiazepines, bisphosphonates, caffeine, calcitonin, calcium-regulating agents, carbamazepine, clonidine, corticosteroids, dantrolene, dexamethasone, disodium pamidronate, ergotamine, flecainide, hydroxyzine, hyoscine, ibuprofen, ketamine, lignocaine, lorazepam, methotrimeprazine, methylprednisolone, mexiletine, mianserin, midazolam, NSAIDs, nimodipine, octreotide, paracetamol, phenothiazines, prednisolone, somatostatin. Suitable opioid analgesic agents are: alfentanil hydrochloride, alphaprodine hydrochloride, anileridine, bezitramide, buprenorphine hydrochloride, butorphanol tartrate, carfentanil citrate, ciramadol, codeine, dextromoramide, dextropropoxyphene, dezocine, diamorphine hydrochloride, dihydrocodeine, dipipanone hydrochloride, enadoline, eptazocine hydrobromide, ethoheptazine citrate, ethylmorphine hydrochloride, etorphine hydrochloride, fentanyl citrate, hydrocodone, hydromorphone hydrochloride, ketobemidone, levomethadone hydrochloride, levomethadyl acetate, levorphanol tartrate, meptazinol hydrochloride, methadone hydrochloride, morphine, nalbuphine hydrochloride, nicomorphine hydrochloride, opium, hydrochlorides of mixed opium alkaloids, papaveretum, oxycodone, oxymorphone hydrochloride, pentamorphone, pentazocine, pethidine hydrochloride, phenazocine hydrobromide, phenoperidine hydrochloride, picenadol hydrochloride, piritramide, propiram fumarate, remifentanil hydrochloride, spiradoline mesylate, sufentanil citrate, tilidate hydrochloride, tonazocine mesylate, tramadol hydrochloride, trefentanil. Illustrative of the application of the invention in relation to formulations for pain relief are formulations containing composite particles comprising fentanyl citrate as analgesic or comprising agents for the treatment of migraine, for example, dihydroergotamine mesylate.

The composite particles could also be used in formulations for the local administration of agents, for example, for anti cancer activity, anti-virals, antibiotics, muscle relaxants, antidepressants, antiepileptics or vaccines.

The term excipient as used herein refers to any solid, generally pharmaceutically inert material which is acceptable for inclusion in pharmaceutical formulations. The excipient material may be composed of one or more materials selected from sugar alcohols; polyols, for example sorbitol, mannitol and xylitol, and crystalline sugars, including monosaccharides and disaccharides; inorganic salts such as sodium chloride and calcium carbonate; organic salts such as sodium lactate; and other organic compounds such as urea, polysaccharides, for example starch and its derivatives; oligosaccharides, for example cyclodextrins and dextrins. Advantageously the excipient material is a crystalline sugar, for example, a monosaccharide such as glucose or arabinose, or a disaccharide such as maltose, saccharose, dextrose or lactose. Preferably, the excipient material is of lactose.

The invention also provides composite excipient particles for use in a pharmaceutical composition, preferably a pharmaceutical composition for inhalation, more preferably a powder for a dry powder inhaler.

The invention further provides composite excipient particles for use in a pharmaceutical composition each composite excipient particle comprising a particle of an excipient material and additive material on the surface of that particle of excipient material, the composite excipient particles having a mass median aerodynamic diameter of less than 20 µm. Preferably, the composite excipient particles have a MMAD of not more than 15 µm, advantageously not more than 10 µm and more preferably not more than 5 µm. Furthermore, 90% by weight of the composite excipient particles may have a diameter of less than 50 µm, advantageously less than 20 µm, more preferably less than 15 µm, more advantageously less than 10 µm and especially advantageously less than 5 µm.

It will be understood that persons skilled in the art are able to convert in an approximate manner between mass, volume, aerodynamic, surface, number based and other diameters.

MMAD may be determined using an impinger, for example, a multi-stage liquid impinger. Volume median diameters and measurements of the proportion of particles having a diameter less than a certain value may be determined by the Malvern laser light scattering method.

The invention further provides a pharmaceutical composition comprising composite excipient particles. Preferably, the pharmaceutical composition is a dry powder and is suitable for use in a dry powder inhaler. Such pharmaceutical compositions may comprise essentially only the composite excipient particles and active particles or they may comprise additional ingredients such as carrier particles and flavouring agents. Carrier particles may be of any acceptable excipient material or combination of materials. For example, the carrier particles may be composed of one or more materials selected from sugar alcohols, polyols and crystalline sugars. Other suitable carriers include inorganic salts such as sodium chloride and calcium carbonate, organic salts such as sodium lactate and other organic compounds such as polysaccharides and oligosaccharides. Advantageously the carrier particles are of a polyol. In particular the carrier particles may be particles of a crystalline sugar, for example, mannitol dextrose or lactose. Preferably, the carrier particles are of lactose.

Advantageously, substantially all (by weight) of the carrier particles have a diameter which lies between 20 μm and 1000 μm, more preferably 50 μm and 1000 μm. Preferably, the diameter of substantially all (by weight) of the carrier particles is less than 355 μm and lies between 20 μm and 250 μm. Preferably at least 90% by weight of the carrier particles have a diameter between from 60 μm to 180 μm. The relatively large diameter of the carrier particles improves the opportunity for other, smaller particles to become attached to the surfaces of the carrier particles and to provide good flow and entrainment characteristics and improved release of the active particles in the airways to increase deposition of the active particles in the lower lung.

The ratio in which the carrier particles (if present), composite excipient particles and active particles are mixed will, of course, depend on the type of inhaler device used, the type of active particles used and the required dose.

Where carrier particles are included in the pharmaceutical composition, the composite excipient particles are preferably present in an amount of from 1% to 40%, more preferably 5% to 20% based on the weight of the carrier particles. The carrier particles are preferably present in an amount of at least 50%, more preferably 60%, advantageously 75% based on the combined weight of the active particles, the composite particles and the carrier particles.

The carrier particles preferably have a relatively highly fissured surface, that is, on which there are clefts and valleys and other recessed regions, referred to herein collectively as fissures. The fissures should preferably be at least 5 µm wide extending to at least 5 µm deep, preferably at least 10 µm wide and 10 µm deep and most preferably at least 20 µm wide and 20 µm deep. The fissured carrier particles offer particular advantages in that they are capable of retaining relatively large amounts of fines (the word "fines" refers to the combined active particles and composite excipient particles) in the fissures without or with only little segregation. That is thought to underly the good respirable fraction that is generated in use of the formulations.

Advantageously, the fines content is not more than 50% by weight, and more preferably not more than 20% by weight, based on the total weight of fines and carrier particles. Preferably, the fines content is at least 5% by weight, based on the total weight of fines and carrier particles. The invention offers particular advantages in the case of formulations containing at least 10%, for example, from 10 to 20% by weight fines or at least 20%, for example from 20 to 50% by weight fines, in each case, based on the total weight of fines and carrier particles. The fines content may include from 0.1 to 90% by weight active particles, and from 0.1 to 99% by weight of composite excipient particles, in each case based on the total weight of fines. In many cases, however, the active particles will constitute less than half of the total weight of fines.

A number of methods may be used to determine whether carrier particles have a fissured surface that will offer the above-mentioned capability of retaining relatively large fines contents substantially without segregation:

1. Determination of Tapped Density.

The tapped density of the fissured carrier particles may be about 6% or more, and preferably 15% or more, lower than the tapped density of carrier particles of the same material and of particle characteristics of a kind typical of carrier particles which have conventionally been used in the manufacture of inhalable powders. In the case of fissured carrier particles of crystalline sugars, for example lactose, the tapped density of the fissured particles is not more than 0.75 g/cm3, and preferably not more than 0.70 g/cm3. The tapped density of lactose grades conventionally used in the manufacture of commercial DPI formulations is typically about 0.8 g/cm3. Tapped densities referred to herein may be measured as follows:

A measuring cylinder is weighed on a top pan balance (2 place). Approximately 50 g powder is introduced into the measuring cylinder, and the weight is recorded. The measuring cylinder containing the powder is attached to a jolting volumeter (Jel Stampfvolumeter). The jolting volumeter is set to tap 200 times. During each tap, the measuring cylinder is raised and allowed to fall a set distance. After the 200 taps, the volume of the powder is measured. The tapping is repeated and the new volume measured. The tapping is continued until the powder will settle no more. The tapped density is calculated as the weight of the powder divided by the final tap volume. The procedure is performed three times (with new powder each time) for each powder measured, and the mean tapped density calculated from those three final tapped volume values.

2. Mercury Intrusion Porosimetry.

Mercury intrusion porosimetry assesses the pore size distribution and the nature of the surface and pore structure of the particles. Porosimetry data is suitably collected over pressure range 3.2 kPa to 8.7 MPa, for example, using an Autopore 9200 II Porosimeter (Micromeritics, Norcross, USA). Samples should be evacuated to below 5 Pa prior to analysis to remove air and loosely bound surface water. Suitable lactose is characterised by a bulk density of not more than 0.65 g/cm3 and preferably not more than 0.6 g/cm3. Suitable lactose is also characterised by a total intrusion volume measured by mercury intrusion porosimetry of at least 0.8 cm3 g-1 and preferably at least 0.9 cm3 g-1. (It has been found that lactose having a bulk density of 0.6 g/cm3 as measured by mercury intrusion porosimetry has a tapped density of about 0.7 g/cm3, whereas the discrepancy between the two methods at lower densities is less.)

3. "Fissure Index".

The term "fissure index" used herein refers to the ratio of a theoretical envelope volume of the particles, as calculated from the envelope of the particles, to the actual volume of the carrier particles, that is, omitting fissures within the envelope. Suitable carrier particles are those having a fissure index of at least 1.25. The theoretical envelope volume may be determined optically, for example, by examining a small sample of the particles using an electron microscope. The theoretical envelope volume of the particles may be estimated via the following method. An electron micrograph of the sample may be divided into a number of grid squares of approximately equal populations, each containing a representative sample of the particles. The population of one or more grids may then be examined and the envelope encompassing each of the particles determined visually as follows. The Feret's diameter for particles within a grid is measured relative to a fixed axis of the image. Typically at least ten particles are measured for their Feret's diameter. Feret's diameter is defined as the length of the projection of a particle along a given reference line as the distance between the extreme left and right tangents that are perpendicular to the reference line. A mean Feret's diameter is derived. A theoretical mean envelope volume may then be calculated from this mean diameter to give a representative value for all the grid squares and thus the whole sample. Division of that value by the number of particles gives the mean value per particle. The actual volume of the particles may then be calculated as follows. First, the mean mass of a particle is calculated. A sample of approximately 50 mg is taken and its precise weight recorded to 0.1 mg. Then by optical microscopy the precise number of particles in that sample is determined. The mean mass of one particle can then be determined. The procedure is then repeated five times to obtain a mean value of this mean. Second, a fixed mass of particles (typically 50 g), is weighed out accurately, and the number of particles within this mass is calculated using the above mean mass value of one particle. Finally, the sample of particles is immersed in a liquid in which the particles are insoluble and, after agitation to remove trapped air, the amount of liquid displaced is measured. From this the mean actual volume of one particle can be calculated. The fissure index is advantageously not less than 1.5, and is, for example, 2 or more.

4. "Rugosity Coefficient".

The rugosity coefficient is used to mean the ratio of the perimeter of a particle outline to the perimeter of the 'convex hull'. This measure has been used to express the lack of smoothness in the particle outline. The 'convex hull' is defined as a minimum enveloping boundary fitted to a particle outline that is nowhere concave. (See "The Shape of Powder-Particle Outlines" A. E. Hawkins, Wiley.) The 'rugosity coefficient' may be calculated optically as follows. A sample of particles should be identified from an electron micrograph as identified above. For each particle the perimeter of the particle outline and the associated perimeter of the 'convex hull' is measured to provide the rugosity coefficient. This should be repeated for at least ten particles to obtain a mean value. The mean rugosity coefficient is at least 1.25.

Carrier particles which have the above-mentioned capability of retaining relatively large amounts of fine material without or with only little segregation will generally comply with all of Methods 1 to 4 above, but for the avoidance of doubt any carrier particles which comply with at least one of Methods 1 to 4 is deemed to be a fissured particle.

The carrier particles are advantageously in the form of an agglomerate consisting of a plurality of crystals fused to one another, the fastness of agglomeration being such that the carrier particles have substantially no tendency to disintegrate on expulsion from the inhaler device. In the case of crystalline sugars, such as lactose, such structures may be obtained in a wet granulation process, in which crystals within an agglomerate become fused to one another by solid bridges, the resultant structure having a complex shape of high irregularity and/or high fractal dimension, including a multiplicity of clefts and valleys, which in some cases may be relatively deep. Each agglomerate will generally contain at least three lactose primary crystals of the characteristic tomahawk shape.

Such agglomerates are clearly distinguished from agglomerates of the kind which form in powder formulations by aggregation of particles, which do tend to disintegrate on expulsion from the inhaler.

Where the carrier particles are fissured carrier particles, they will preferably have a MMAD of at least 175 μm, more preferably at least 200 μm.

Suitably shaped carrier particles also include dendritic spherulites of the type disclosed in U.S. Pat. No. 4,349,542 for use in tablet manufacture.

Where the pharmaceutical composition is a powder for use in a dry powder inhaler and does not comprise carrier particles the composite excipient particles are preferably present in an amount of at least 1%, more preferably at least 5%, advantageously at least 10% and most preferably at least 20% by weight based on the combined weights of the composite excipient particles and the active particles. The composite excipient particles will preferably be present in an amount of not more than 95%, more preferably not more than 90% and especially advantageously not more than 70% based on the combined weights of the composite excipient particles and the active particles.

The pharmaceutical composition may comprise a propellant and be suitable for use in a pressurised metered dose inhaler.

The invention also provides the use of an additional material as a milling aid in the milling of particles of an excipient material. The term milling aid should be understood to refer to a substance which reduces the amount of energy required to mill the particles of excipient material.

Embodiments of the invention will now be described for the purposes of illustration only.

Evaluation of the fine particle fraction of multi-stage liquid impinger (MSLI) was carried out in accordance with method given in European Pharmacopoeia, Supplement 2000, Section 2.9.18.

Evaluation of the fine particle fraction using a twin stage liquid impinger (TSI) was carried out in accordance with the method of WO 96/23485 pages 29 to 33. The method is also described in the European Pharmacopoeia referred to above and in J. Pharm. Pharmacol, 1987, 39, 966-972).

All percentages are by weight unless indicated otherwise.
Composite Excipient Particles Method 1

98 g of Microfine (MMAD approximately 8 μm) lactose (manufactured by Borculo) was placed in a stainless steel milling vessel. 300 g of stainless steel milling balls varying from 10 to 3 mm diameter were added. 2 g of additive material was added and the vessel was located in a Retsch S100 Centrifugal Mill. The powder was milled for 30 minutes at 580 rpm and was then sieved to remove the milling balls. Each of the following additive materials were used in turn: magnesium stearate, calcium stearate, sodium stearate, lithium stearate, stearic acid, stearylamine, soya lecithin, sodium stearyl fumarate, 1-leucine, 1-iso-leucine, oleic acid, starch, diphosphatidyl choline, behenic acid, glyceryl behenate and sodium benzoate. Pharmaceutically acceptable fatty acids and derivatives, waxes and oils may also be used (where those materials are sticky, they should be used at levels where their stickiness does not inhibit the flow of the powder).

Method 2

95 g of Microfine lactose (Borculo) was placed in a ceramic milling vessel (manufactured by the Pascall Engineering Company). 5 g of additive material and the ceramic milling balls were added. The ball mill was tumbled at 60 rpm for 5 hours. This was repeated a number of times with the amount of additive material varied as a percentage of the lactose from 0.25 to 20%. Additive materials used were L-leucine and magnesium stearate.

The powder was recovered by sieving to remove the milling balls.

Method 3

Experiments were performed to produce co-processed powders of fine lactose and additive material (l-leucine) in a Gem-T jet mill. Quantities of L-leucine were varied from 0.5 to 10% based on the weight of the lactose. Lactoses used included Lactochem Regular (having a broad distribution of particle sizes over 1-200 μm) and Microfine (Borculo). The mill was operated normally.

Method 4

Method 3 was repeated using magnesium stearate in place of l-leucine.

Method 5

The experiments of Methods 3 and 4 were repeated using a Retsch ZM100 Ultra-Centrifugal Mill.

Method 6

Leucine was micronised in a jet mill and blended with Microfine lactose (Borculo) in a high shear mixer (Morphy Richards food processor) or in a Retsch ZM100 Ultra-Centrifugal mill. Quantities of L-leucine were varied from 0.5 to 10% based on the weight of the lactose.

Methods 3, 5 and 6 (where leucine is used) are less favoured methods, as the powders frequently performed only slightly better than with equivalent powders comprising unmodified lactoses. This is believed to be because the mills used were not sealed allowing the leucine to escape as fine particles or as vapour. In method 4, (using magnesium stearate, which is not as volatile as leucine), the powders performed well.

It was observed in some cases that when ball milling according to Methods 1 and 2, a fine powder was not produced. Instead the powder was compacted on the walls of the mill by the action of the mill. That inhibited the milling action and prevented the preparation of the composite excipient particles. That problem occurred particularly when certain additive materials were used, in cases where the additive material was present in small proportions (typically <2%), in cases where the milling balls were relatively small (typically <3 mm), in cases where the milling speed was too slow and where the starting lactose was too fine. To prevent this occurring it is advantageous to mill in a liquid medium. The liquid medium reduces the tendency to compaction, assists the dispersal of additive material with lactose and improves any milling action.

Method 7

2 g leucine with 98 g of ultra-fine micronised lactose (mass median diameter approximately 3 μm) was placed in a stainless steel milling vessel. 300 g of stainless steel milling balls varying from 10 to 3 mm diameter were added. The vessel was located in a Retsch 5100 Centrifugal Mill. The powder was milled for 10 minutes at 580 rpm and was found to have compacted on the sides of the vessel, and consequently co-milling was not possible. Compaction also occurred when magnesium stearate was used as additive material. Sufficient cyclohexane was added to the vessel to create a loose paste and the co-milling was continued successfully in that liquid medium. The excipient powder was recovered by drying the paste, milling the powder for 2 minutes and sieving.

Method 8

10 g of Microfine lactose (Borculo) was combined with 1 g of sodium stearate and 10 cm3 cyclohexane. 50 g of 5 mm balls were added and the mixture was milled for 90 minutes. The powder was recovered by leaving the paste in a fume hood overnight to evaporate the cyclohexane and then ball milling for 1 minute. Powders having lecithin, PVP, Span 80, magnesium stearate and leucine in place of sodium stearate were prepared by this method. Quantities of additive material were usually 10% by weight based on weight of lactose but were also varied from 1% to 60%. The experiments were also repeated using dichloromethane as liquid medium.

Method 9

47.5 g of Sorbalac 400 (Meggle) was combined with 2.5 g of magnesium stearate and 50 cm3 dichloromethane. 620 g 3 mm stainless steel balls were added to the mixture and the mixture was milled in a 250 cm3 stainless steel pot at 500 rpm for 90 minutes in a Retsch 5100 Centrifugal mill.

The excipient powder was recovered by drying the paste, milling the powder for 2 minutes and sieving to remove the steel balls.

This method was repeated using leucine in place of magnesium stearate.

Pharmaceutical Compositions Comprising Composite Excipient Particles

Composition 1

0.9 g of composite excipient particles made by method 2 containing 5% l-leucine in Microfine lactose was blended with 0.6 g of micronised budesonide by hand in a mortar. This blending could also be performed, for example, in a high shear blender, or in a ball mill or in a centrifugal mill. The resulting powder may be used in an inhaler directly, although in this example a sample of this powder was blended with a coarse carrier lactose (355 to 600 μm) by tumbling in order to improve the powder flow properties. The powder was fired from a Cyclohaler at a flow rate of 60 liter per minute in a multi-stage liquid impinger. The fine particle fraction (<5 μm) was 45%.

Composition 2

1 of micronised salbutamol sulphate was added to 1 g of composite excipient particles made by method 1 containing 2% lecithin, and to 8 g of a coarse carrier lactose. The mixture was tumbled for 30 minutes at 42 rpm. The resulting power was fired from a Cyclohaler at a flow rate of 60 liters per minute into a twin-stage impinger, giving a fine particle fraction (<5 microns) of about 44%. A similar example with a 2% leucine precursor gave a fine particle fraction (<5 μm) of 52%.

Composition 3

The wet milled composite excipient particles have given particularly good results.

0.5 g of micronised salbutamol sulphate was added to 0.5 g of composite excipient particles made by method 7 containing 10% magnesium stearate, and to 4 g of a coarse carrier lactose. This was tumbled for 30 minutes at 62 rpm. The resulting powder was fired from a Cyclohaler at a flow rate of 60 liters per minute into a twin-stage impinger, giving a fine particle fraction (<5 μm) of 57%. The experiment was repeated using composite excipient particles containing 20% magnesium stearate and similar results were obtained.

Composition 4

0.5 g of micronised salbutamol sulphate, 0.25 g of g of composite excipient particles made by method 7 containing 10% magnesium stearate, 0.25 g of g of composite excipient particles made by method 7 containing 10% leucine, and 4 g of a coarse carrier lactose were all combined. The mixture was tumbled for 30 minutes at 62 rpm. The resulting powder was fired from a Cyclohaler at a flow rate of 60 liters per minute into a twin-stage impinger, giving a fine particle fraction (<5 μm) of ~65%.

Composition 5

0.5 g of micronised salbutamol sulphate, 0.25 g of composite excipient particles made by method 7 containing 10% lecithin, 0.25 g of composite excipient particles made by method 7 containing 10% leucine, and 4 g of a coarse carrier lactose were combined. The mixture was tumbled for 30 minutes at 62 rpm. The resulting powder was fired from a Cyclohaler at a flow rate of 60 liters per minute into a twin-stage impinger, giving a fine particle fraction (<5 μm) of 68%.

Composition 6

0.5 g of micronised salbutamol sulphate, 0.25 g of composite excipient particles powder made by method 7 containing 10% lecithin, and 0.25 g of g of composite excipient particles powder made by method 7 containing 10% sodium stearate, and 4 g of a coarse carrier lactose were combined. The mixture was tumbled for 30 minutes at 62 rpm. The resulting powder was fired from a Cyclohaler at a flow rate of 60 liters per minute into a twin-stage impinger, giving a fine particle fraction (<5 μm) of 65%.

Composition 7

0.25 g micronised Fentanyl citrate, 5 g of composite excipient particles made by method 9 and 44.75 g of Prismalac (Meggle) 355-600 μm sieve fraction lactose were combined in a Turbula mixer for 30 minutes at 60 rpm. The resulting powder was fired from a Cyclohaler at a flow rate of 90 liters min-1 into a multistage liquid impinger giving a fine particle fraction (<5 μm) of approximately 50%.

Composition 8

Composition 7 was repeated using double quantities of each material and replacing fentanyl citrate with micronised budesonide. The fine particle fraction was approximately 50%.

Composition 9

Composition 8 was repeated using micronised dihydroergatamine mesylate in place of the budesonide. The fine particle fraction was approximately 60%.

It has been found to be particularly favourable to use a 355 to 600 μm sieve fraction of Prismalac as the coarse carrier lactose. Segregation has not been observed in those formulations, even those comprising 10 and 20% magnesium stearate (i.e. up to 2% in the final composition).

When milling excipient material, it has been found to be preferable to use a large number of fine milling balls, rather than fewer heavy balls. The finer balls perform a more efficient co-milling action. Preferably the balls have a diameter of 5 mm or less, advantageously 2 mm or less. Liquid media are preferred which do not dissolve the excipient material and which evaporate rapidly and fully, for example non-aqueous liquids such as cyclohexane, ethanol, isopropanol or dichloromethane. Liquid media are preferred which are non flammable, for example dichloromethane and fluorinated hydrocarbons, especially fluorinated hydrocarbons which are suitable for use as propellants in inhalers.

A particularly preferred method is milling using a high pressure homogeniser, as this reduces contamination as compared to ball milling, for example, where the collisions between the balls may produce contaminants.

In the wet milling process, the additive material appears to confer several advantages: it allows the milling process to be more efficient, with smaller particles produced and compaction reduced, the particles may be stabilised in suspension, and on drying, the ternary agent remains as a coating around the particles which may aid dispersion, and may modify the subsequent dissolution characteristics of the particle.

When the active material is a protein, the milling may be preceded by lyophilisation (freeze drying) of the protein either pure or in combination with an additive material and/or a polymeric stabiliser. The freeze drying may make them more brittle and more easily milled. The milling may need to be conducted under cryogenic (cold) conditions to increase the brittleness of the material.

The invention claimed is:

1. Composite excipient particles for use in a pharmaceutical composition, each composite excipient particle comprising a particle of an excipient material and additive material adhering to the surface of that particle of excipient material, wherein 90% by weight of the composite excipient particles have diameter of less than 20 μm determined using the Malvern laser light scattering method, wherein the additive material is in the form of particles coating the surfaces of the particles of excipient material.

2. The composite excipient particles as claimed in claim 1, wherein 90% by weight of the composite excipient particles have a diameter of less than 15 μm.

3. The composite excipient particles as claimed in claim 1, wherein 90% by weight of the composite excipient particles have a diameter of less than 10 μm.

4. The composite excipient particles as claimed in claim 1, wherein the excipient material is a crystalline sugar.

5. The composite excipient particles as claimed in claim 1, in which the additive material comprises an amino acid.

6. The composite excipient particles as claimed in claim 1, in which the additive material comprises a phospholipid.

7. The composite excipient particles as claimed in claim 1, in which the additive material comprises a metal stearate.

8. A pharmaceutical composition comprising composite excipient particles as claimed in claim 1, and active particles.

9. The pharmaceutical composition as claimed in claim 8, wherein the active particles comprise one or more of a $\beta_2$-agonist, ipatropium bromide, a steroid, a cromone, heparin, DNAse, leukotrienes, or insulin.

10. The pharmaceutical composition as claimed in claim 8, which is a dry powder and is suitable for use in a dry powder inhaler.

11. The pharmaceutical composition as claimed in claim 8, which comprises carrier particles.

12. The pharmaceutical composition as claimed in claim 11, which comprises the composite excipient particles in an amount of 1 to 40% based on the weight of the carrier particles.

13. The pharmaceutical composition as claimed in claim 11, in which the carrier particles have a fissured surface.

14. The pharmaceutical composition as claimed in claim 13, in which the carrier particles are of a crystalline sugar having a tapped density not exceeding 0.75 g/cm$^3$.

15. The pharmaceutical composition as claimed in claim 13, in which the carrier particles have a bulk density as measured by mercury intrusion porosimetry of not exceeding 0.6 g/cm$^3$.

16. The pharmaceutical composition as claimed in claim 11, in which the carrier particles have a MMAD of at least 175 μm.

17. The pharmaceutical composition as claimed in claim 8, which comprises a propellant and is suitable for use in a pressurised metered dose inhaler.

18. A dry powder inhaler comprising a pharmaceutical composition as claimed in claim 8.

19. A pressurised metered dose inhaler comprising a pharmaceutical composition as claimed in claim 17.

* * * * *